US00PP08868P

United States Patent [19]

VandenBerg

[11] Patent Number: Plant 8,868

[45] Date of Patent: Aug. 23, 1994

[54] CHRYSANTHEMUM PLANT NAMED HONEY MONTEREY

[75] Inventor: Cornelis P. VandenBerg, Salinas, Calif.

[73] Assignee: Yoder Brothers, Inc., Chualar, Calif.

[21] Appl. No.: 99,662

[22] Filed: Jul. 30, 1993

[51] Int. Cl.[5] ..... A01H 5/00

[52] U.S. Cl. ..... Plt./82.2

[58] Field of Search ..... Plt. 82.2, 82.4

[56] References Cited

U.S. PATENT DOCUMENTS 4,616,099 10/1986 Sparkes ..... 47/58

OTHER PUBLICATIONS

Broertjes, et al., 1980, "A Mutant of a mutant of a . . . Irradiation of progressive radiation-induced mutants in a mutation breeding programme with *Chrysanthemum morifolium*", Euphytica, 29:526–530.

Gosling, ed., 1979, "The Chrysanthemum Manual—6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by X-rays", Am. Soc. Hort. Sci. Proc., pp. 613–620.

Broertjes, 1966, "Mutation breeding of Chrysanthemums", Euphytica, 15:156–162.

Dowrick et al., 1966, "The induction of mutations in Chrysanthemum using X- and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Honey Monterey particularly characterized by its flat capitulum form; daisy capitulum type; yellow-orange ray floret color; diameter across face of capitulum of 76 to 89 mm when fully opened, when grown as a pinched spray pot mum; photoperiodic flowering response to short days of 54 to 61 days; plant height, with 14 to 17 long days after sticking unrooted cuttings, and with 1 to 2 applications of 2500 ppm B-9 SP, ranges from 18 to 25 cm when grown as a pinched pot mum with 4 cuttings in a 15 cm pot; branching pattern is semi-spreading, each plant having 3 to 5 laterals after pinch; and recommended as spray pot mum.

1 Drawing Sheet

The present invention comprises a new and distinct cultivar of Chrysanthemum, botanically known as *Dendranthema grandiflora,* and referred to by the cultivar name Honey Monterey.

Honey Monterey, identified as 5753 (86-420A02), is a product of a mutation induction program.

Honey Monterey was discovered and selected by Cornelis P. VandenBerg on Feb. 21, 1991 in a controlled environment in Salinas, Calif. in comparative flower trials of selections of radiation sports originating from irradiation of the cultivar identified as Monterey, disclosed in U.S. Plant Pat. No. 7,753 and described as a spray pot mum with a flat capitulum form; a daisy capitulum type; a soft lavender pink ray floret color; diameter across face of capitulum of 83 to 95 mm when fully opened; flowering response period of 52 to 60 days after start of short days; plant height of 18 to 30 cm when grown as a pinched spray pot mum with 15 to 18 long days after sticking unrooted cuttings prior to start of short days with 1 to 2 applications of 2500 ppm B-9 SP; and semi-spreading branching pattern, with 3 to 5 laterals after pinch. One selection in these comparative flower trials was identified by the code number 4196, which was selected in June 1990 as one flowering plant within a flowering block established as rooted cuttings from stock plants of Monterey which had been exposed as unrooted cuttings to an X-ray source of 1750 rads in Fort Myers, Fla., on Dec. 14, 1989. Repeated flowerings of code 4196 showed a mixture of plants with different ray floret color. One plant with a honey-bronze ray floret color was selected on Feb. 21, 1991 and given the code number 5753 (86-420A02), and subsequently the cultivar name Honey Monterey.

The irradiation program resulting in code 4196 and ultimately in Honey Monterey had as its primary objective the expansion of color ranges of the parent cultivar Monterey. The irradiation program comprised irradiating cuttings of the parent cultivar at irradiation levels of 1750 and 2000 rads. A total of 612 cuttings harvested from a total of 150 irradiated plants were planted on Apr. 23 and Apr. 16, 1990. Of these, 5 initial selections were made, which selections were then revegetated and reflowered. Three consecutive flowerings resulted in discarding 4 of the original 5 selections on Mar. 13, 1991. The one remaining selection, 4196, was reselected as 5753. 4196 was subsequently discarded on Apr. 1, 1991, while the decision was made to introduce 5753 as Honey Monterey.

The first act of asexual reproduction of Honey Monterey was accomplished when vegetative cuttings were taken from the reselected selection in May 1991 in a controlled environment in Salinas, Calif., by technicians working under supervision of Cornelis P. VandenBerg.

Horticultural examination of controlled flowerings of successive plantings has shown that the unique combination of characteristics as herein disclosed for Honey Monterey are firmly fixed and are retained through successive generations of asexual reproduction.

Honey Monterey has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Honey Monterey, which, in combination, distinguish this Chrysanthemum as a new and distinct cultivar.

1. Flat capitulum form.
2. Daisy capitulum type.
3. Yellow-orange ray floret color.
4. Diameter across face of capitulum of 76 to 89 mm when fully opened, when grown as a pinched spray pot mum.
5. Photoperiodic flowering response to short days of 54 to 61 days.
6. Plant height, with 14 to 17 long days after sticking unrooted cuttings and with 1 to 2 applications of 2500 ppm B-9 SP, ranges from 18 to 25 cm when grown as a pinched pot mum with 4 cuttings in a 15 cm pot.
7. Branching pattern is semi-spreading, each plant having 3 to 5 laterals after pinch.
8. Recommended as spray pot mum.

The accompanying photographic drawing is a side view of a potted mum of Honey Monterey, with 4 cuttings in a 15 cm pot, with the colors being as nearly true as possible with illustrations of this type.

Of the commercial cultivars known to the inventor, the most similar in comparison to Honey Monterey is the parent cultivar Monterey. Most traits of Honey Monterey are similar to those of Monterey, except for the ray floret color, flowering response to short days and diameter of capitulum. Monterey has a soft lavender pink ray floret color, while Honey Monterey has an yellow-orange ray floret color. In addition, flowering response time to short days of Honey Monterey has been observed to be one to two days slower than Monterey in several flowering trials. The diameter of capitulum of Honey Monterey is 3 to 7 mm smaller than the diameter of capitulum of Monterey.

In the following description color references are made to the Royal Horticultural Society Colour Chart. The color values were determined on plant material grown as a pinched spray pot mum in Salinas, Calif. on Oct. 29, 1992.

Classification:

*Botanical.*—*Dendranthema grandiflora* cv Honey Monterey.

*Commercial.*—Flat daisy spray pot mum.

INFLORESCENCE

A. Capitulum:

*Form.*—Flat.

*Type.*—Daisy.

*Diameter across face.*—76 to 89 mm when fully opened.

B. Corolla of ray florets:

*Color (general tonality from a distance of three meters).*—Yellow-orange.

*Color (upper surface).*—Closest to 17C.

*Color (under surface).*—Closest to 17D.

*Shape.*—Straight, pointed, slightly ribbed. Apex slightly indented.

C. Corolla of disc florets:

*Color (mature).*—12A.

*Color (immature).*—144C.

D. Reproductive organs:

*Androecium.*—Present on disc florets only; no pollen.

*Gynoecium.*—Present on both ray and disc florets.

PLANT

A. General appearance:

*Height.*—18 to 25 cm when grown as a pinched pot mum with 14 to 17 long days prior to start of short days, with 1 to 2 applications of 2500 ppm B-9 SP.

*Branching pattern.*—Semi-spreading, with 3 to 5 laterals after pinch.

B. Foliage:

*Color (upper surface).*—147A.

*Color (under surface).*—147B.

*Shape.*—Deeply lobed, slightly serrated.

I claim:

1. A new and distinct Chrysanthemum plant named Honey Monterey, as described and illustrated.

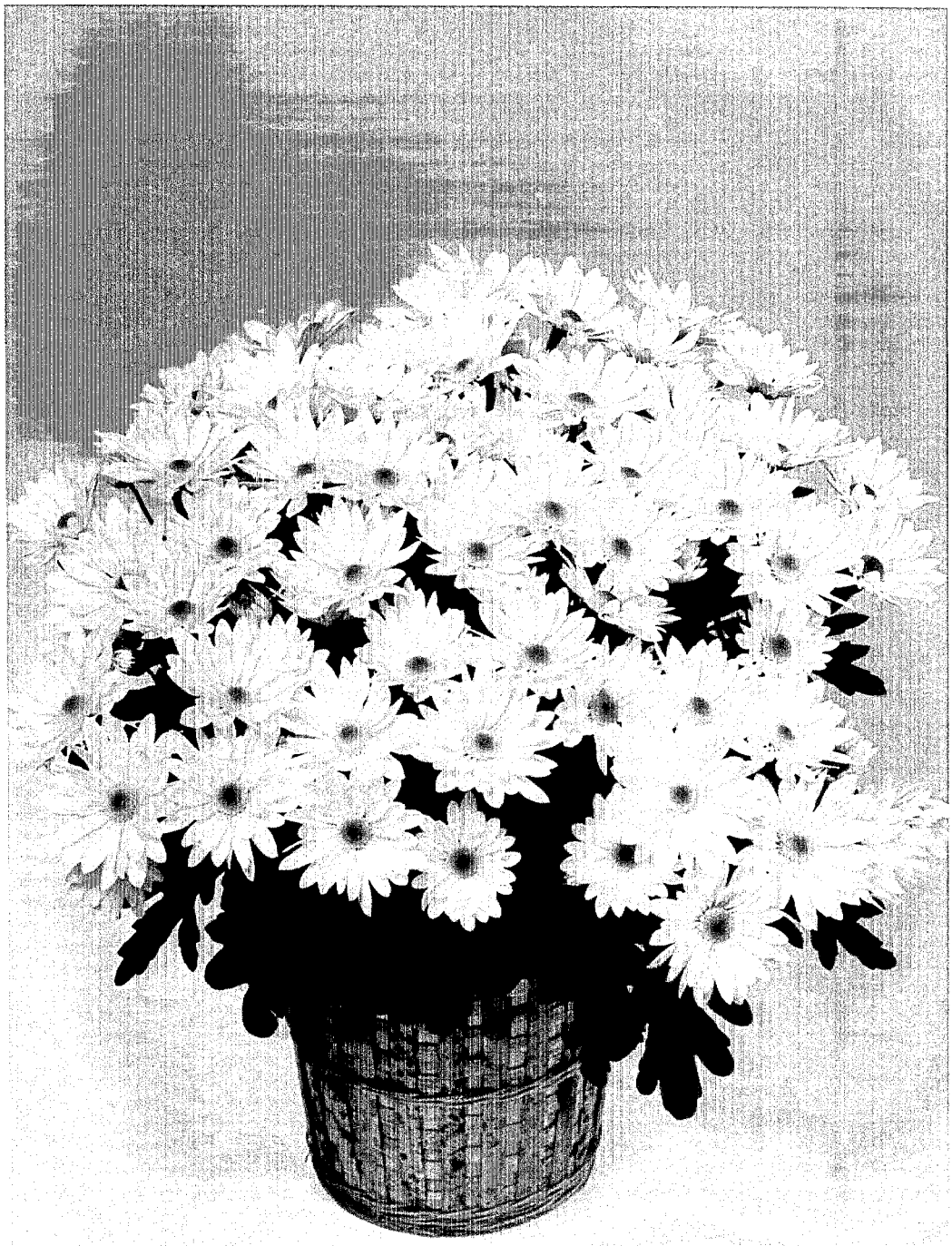

* * * * *